United States Patent [19]

Ishida et al.

[11] 4,067,801

[45] Jan. 10, 1978

[54] PROCESS AND SYSTEM FOR ANAEROBIC TREATMENT OF BIOCHEMICAL WASTE

[75] Inventors: Masahiko Ishida; Ryooichi Haga; Youji Odawara, all of Hitachi, Japan

[73] Assignee: Hitachi, Ltd., Japan

[21] Appl. No.: 685,901

[22] Filed: May 12, 1976

[30] Foreign Application Priority Data

May 14, 1975 Japan .................................. 50-56151
May 19, 1975 Japan .................................. 50-58522
July 4, 1975 Japan .................................. 50-81808

[51] Int. Cl.$^2$ ............................................. C02C 1/14
[52] U.S. Cl. ........................................ 210/5; 210/180; 210/195 S
[58] Field of Search .................... 210/2, 4, 5, 16, 170, 210/195 S, 180, 197

[56] References Cited

U.S. PATENT DOCUMENTS

| | | |
|---|---|---|
| 2,029,702 | 2/1936 | Buswell .................................. 210/4 |
| 3,468,794 | 9/1969 | Amero .................................... 210/4 |
| 3,838,199 | 9/1974 | Coe ...................................... 210/2 X |
| 3,981,800 | 9/1976 | Ort ...................................... 210/16 X |

*Primary Examiner*—Sidney Marantz
*Attorney, Agent, or Firm*—Craig & Antonelli

[57] ABSTRACT

In a system for treatment of biochemical waste such as activated sludges, the waste is subjected to anaerobic stabilization processes, which include two phases of an acid fermentation and a methane fermentation effected in separate reactors. The waste after the acid fermentation is then separated into a liquid effluent for the methane fermentation and a waste sludge. The waste sludge which may cause secondary environmental pollution is re-treated within the anaerobic stabilization processes without withdrawing from the system.

22 Claims, 4 Drawing Figures

PROCESS AND SYSTEM FOR ANAEROBIC TREATMENT OF BIOCHEMICAL WASTE

BACKGROUND OF THE INVENTION

The present invention relates to a process and system for treatment of biochemical waste and more particularly to a process and system for anaerobic digestion of biochemical waste.

Recently, with the increase of equipments of secondary treatment of sewage and waste from the livestock industries, large quantity of surplus sludge is formed as by-products. Further, quantities of household garbage is considerably large. Accordingly, it is important to treat the biochemical waste with high effeciency without causing environmental pollution. The biochemical waste is now disposed of by incinerations, reclamations and dumping into the sea. However, it is known that secondary pollution is readily caused by these disposals. As local regulations on reclamations and dumping into the sea have been made strict, the inclinating method has now spread far and wide. However, this method involves various problems as to the treatment of smokes, bad smells and ashes formed by burning.

Biochemical waste such as activated sludges has been treated by anaerobic stabilization processes. It is known that the anaerobic stabilization processes are defined in terms of sequences involving two main reactions. More specifically, it involves an "acid fermentation" in which the molecular weights of the organic substances in the waste are reduced by anaerobic acid fermentation bacteria (acid formers, put refractive bacteria) and the substances are converted to volatile organic acids such as acetic acids, propionic acids and butyric acids, and a "methane fermentation" in which the so-formed organic acids are converted to methane gas by methane fermentation bacteria (methane formers, methane producing bacteria).

In conventional practice of the anaerobic stabilization processes, both phases of acid fermentation and methane fermentation co-exist within the same physical and chemical environment and process efficiency and control requirement are determined by the sensitivity and kinetic characteristics of the rate limiting phase. Accordingly, such a long period as thirty to fifty days is generally required for accomplishment of the anaerobic stabilization processes. However, the pollution preventing and energy saving characteristics of the anaerobic stabilization processes are recently reconsidered and many research efforts are being made to improve the fatal defect of these processes, i.e., a low treatment efficiency.

Recently, as a result of experiments using model wastes, it was proved that the above two fermentation phases can be separated from each other, and by this two-phase anaerobic stabilization process under optimum conditions, the treatment time can be remarkably shortened over the conventional process, which is written in "Developments in Anaerobic Treatment Processes" (Biotechnol. & Bioeng. Symp. No. 2 Page 85 to 106 1971, F. G. Pohland and S. Ghosh). In this two-phase process, the treated waste which has been subjected to the acid fermentation is separated into supernatant liquid containing organic acids and waste sludge by some solid-liquid separation units. The supernatant liquid is transferred to the methane fermentation stage and treated therein by methane formers.

The waste sludge separated after the acid fermentation is partly recycled to the acid fermentation stage and the remainder of the waste sludge is withdrawn from the treatment system.

We reproduced the two-phase treatment system, and found that the treatment efficiency can be improved but the gas yield is reduced by 10 to 30% as compared with the conventional process. We elucidated this cause and found that the reduction of the gas yield is due to the fact that parts of the waste sludge including cells of acid formers formed as by-products, separated after the acid fermentation is withdrawn from the system. In the anaerobic treatment of biochemical waste, it is important to improve the treatment efficiency, but in view of great demand for saving energy, it is desirable to increase the gas yield so as to utilize the digestion gases formed as by-products for heat and power sources of treatment equipments and utilize excessive gases effectively for other purposes. Further, as cells of acid formers include volatile organic acids such as acetic acids, propionic acids and n-butyric acids and typical bad smell producing components such as $H_2S$, it is not preferred to withdraw the waste sludges including the cells outside the system after the acid fermentation.

SUMMARY OF THE INVENTION

One object of the present invention is to provide an improved process and system for anaerobic treatment of biochemical waste with high treatment efficiency.

Another object of the present invention is to provide an improved process and system for anaerobic treatment of biochemical waste with high gas productivity.

Still another object of the present invention is to provide an improved process and system for anaerobic treatment of biochemical waste, which eliminates secondary environmental pollutions.

According to the present invention, biochemical waste such as activated sludges, is subjected to anaerobic stabilization processes, which include two phases of an acid fermentation and a methane fermentation. Both two phases are effected in separate reactors and waste sludge including acid formers after the acid fermentation is retreated within the anaerobic stabilization processes.

According to the present invention, it is preferable to recover the cells of acid formers from the waste after the acid fermentation so as to enhance the efficiency of the stabilization process.

Further, it is preferable to recycle the waste sludge for further fermentation so as to enhance the efficiency of the stabilization process.

According to another feature of the present invention, it is preferable that the biochemical waste is subjected to a preliminary treatment prior to the acid fermentation.

DESCRIPTION OF PREFERRED EMBODIMENTS

Figure 1:
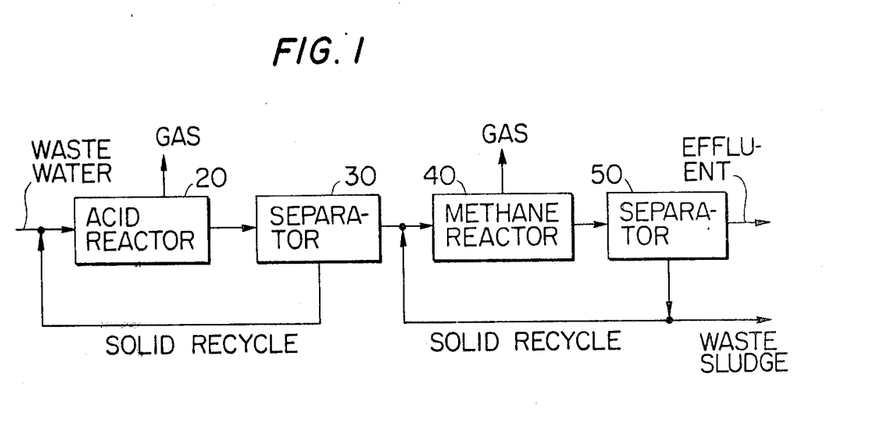
FIG. 1 is a block diagram showing a basic feature of the anaerobic stabilization process of the present invention.

Referring to FIG. 1 of the drawings, biochemical waste water including waste such as activated sludge, garbage, raw sewage, waste water from alcohol distillation processes or concentrated waste water discharged from food manufacturing processes is introduced to an acid reactor 20 for acid fermentation, in which the waste is contacted with acid fermentation bacterias and anaerobically maintained at a prescribed temperature for several days. While the acid fermentation is effected in the acid reactor 20, macromolecular substances are converted to low molecular weight substances and further decomposed into volatile organic acids. It is preferred to keep the waste within the acid reactor 20 at a temperature of 30° to 50° C and a pH of 3 to 7. These temperature and pH conditions are appropriately chosen depending on the kinds of the waste and bacteria used. It is especially preferred that during the acid fermentation. the pH in the reactor 20 be adjusted to a suitable level by adding a neutralizing agent such as NaOH, KOH, $Na_2CO_3$, $Ca(OH)_2$ or $CaCO_3$. The agitation and temperature controls are performed by conventional methods used for anaerobic stabilization processes; for example, a gas agitation, a mechanical agitation method, a method using heat exchanger and a direct vapor blowing method. As acid formers, acid fermentation bacteria belonging to the genera of Clostridum, Escherichia, Bacillus and Staphyloccus are used. In general, two or more kinds of bacteria are employed at the same time. However, a single species of bacteria can be employed as acid formers. After the acid fermentation has completed, the waste is introduced in a separator 30 wherein the waste is separated into supernatant liquid and waste solid by a solid-liquid separation method such as sedimentation separation method, a low speed centrifugal separation method or a filtration method. The solid including the cells of acid fermentation bacteria and undigested residue partly are recycled to the acid reactor 20. The supernatant liquid (which contains the volatile organic acids) is introduced in a methane reactor 40 for methane fermentation, in which the volatile acids are converted to methane gas and carbon dioxide gas. In order to perform this methane fermentation, it is preferred to heat the supernatant liquid at 30° to 50° C under an anaerobic atmosphere while sufficiently agitating and adjusting the pH 7 to 8. Heating and agitating can be accomplished by the method described above with respect to the acid fermentation. Adjustment of pH is accomplished by adding a mineral acid or an organic acid. As the methane formers, there can be used any known methane fermentation bacteria such as methane fermentation bacterias belonging to the genera of Metanosarcina, Metanococcus and Metanobacterium.

The gas produced while methane fermentation comprises 60 to 90% of methane as main components and 10 to 40% of carbon dioxide, and minute amounts of $H_2S$, $N_2$ and $H_2$. The gas produced while methane fermentation is mixed with the gas produced while acid fermentation and used as a heat source for the temperature control of the treatment system and a power source for agitation.

The waste after completion of the methane fermentation in the methane reactor 40 is separated into supernatant liquid and waste solid. The supernatant liquid is discharged as effluent. The waste solid is withdrawn as waste sludge and dehydrated, dried and then used for organic fertilizers. In order to further enhance the treatment efficiency of the stabilization process, a part of the waste solid may be recycled in the acid reactor 40.

A preferred embodiment of the present invention will now be described with reference to FIG. 2 of the drawings. In this embodiment, a preliminary treatment of the waste is conducted. The waste in a raw material tank 11 is introduced to a pretreatment tank 12 through a pipe 101 before acid fermentation, where the waste is preliminarily treated at a pH of 1.0 to 3.0 while heating, by a heater 13.

An ordinary biochemical waste including activated sludge is a kind of a hydrophilic colloid having a state that resembles a state of a hydrated gel, and it has a solid concentration of about 5% and takes a slurry or pasty form. Therefore, a large agitation power is required for digestion. Even in the case of such a biochemical waste, by performing a heat treatment under acid conditions, macromolecular components are modified and partially decomposed to reduce the viscosity of the waste, the subsequent digestion processes can be facilitated and both the digestion efficiency and the gas yield can be highly improved. In this preliminary treatment, good effects are obtained when the pH is lower than 3.5. The lower the pH in the pretreatment tank, the higher the effect of the preliminary treatment. However, from the economical view point, it is preferred that the preliminary treatment be conducted at a pH of 1.0 to 3.0. Not only mineral acids such as sulfuric acid and hydrochloric acid but also organic acids such as acetic acid and citric acid are effectively used for this acidification. From the economical view point, sulfuric acid and hydrochloric acid are preferable. Further, high concentration acids are preferable because troubles caused by the use of dilute acids are prevented. The amount of acids added changes considerably depending on the kind of solid content of the raw materials and the kind and concentration of the acids used. In general, in order to obtain the above preferred pH condition, for example, 35% HCl can be added in an amount of 0.1 to 1% weight/weight of waste.

The reduction of the viscosity can not be obtained by a preliminary treatment under neutral condition at a high temperature of above 150° C. By a preliminary treatment under alkaline conditions, the viscosity is rather increased and it is necessary that the heating should be conducted at a temperature of at least 60° C for at least 1 minute. However, if the treatment is conducted at excessively higher temperature for a long period, for example at 170° C for 20 minutes, decomposition products inhibiting the digestion are formed. Accordingly, the preliminary treatment is preferably conducted at a temperature not higher that 160° C for 10 minutes at the longest under acid conditions. However, the preliminary treatment can be omitted for simplifying the system. Further, when the waste contains large solid, it is preferable to pulverize the waste to slurry prior to the acid fermentation.

The waste in which has been subjected to this preliminary treatment is then introduced to an acid fermentation reactor 21 through a pipe 102 and contacted with acid formers under an anaerobic condition. After the acid fermentation is completed the waste containing the undigested residue the cells of acid formers and the volatile organic acids is introduced into a first settling tank 31 through a pipe 103; in which the undigested residue is separated by a solid-liquid separation method from the supernatant liquid including cells of acid formers and the volatile organic acids. The supernatant liquid thus separated is introduced into a heat treatment tank 32 through a pipe 104 and the cells of acid formers are heated by a heater 34 to physiologically deactivate and form an agglomeration of cells. In order to obtain a good agglomeration, it is necessary to conduct the heat treatment at a temperature at least 70° C for at least 1 minute. Further, a good agglomeration and sedimentation can be obtained when the pH is in a region from 3 to 9, and if at least 200 ppm of $Ca^{2+}$, $Mg^{2+}$ or $Al^{3+}$ are present, the agglomeration and sedimentation can be accomplished very easily. As the Ca agent, there can be employed calcium hydroxide, calcium chloride, calcium carbonate, calcium nitrate and organic acid salts of calcium. The agglomerated cells of the acid formers are introduced in a second settling tank 33 through a pipe 105 and are sedimented therein. Thus the sedimented cells are separated from the supernatant liquid including volatile organic acid and returned to the acid fermentation reactor 21 through a pipe 110 and 111. Further the sedimented cells can be introduced to the preliminary treatment tank 12 through the pipe 110 and a pipe 112.

The supernatant liquid in the settling tank 33 is sent into a methane fermentation reactor 41 through a pipe 106, wherein the supernatant liquid is contacted with methane formers for methane fermentation under an anaerobic condition and the volatile organic acids in the supernatant liquid are converted to methane gas and carbon dioxide gas.

Also the undigested residue separated in the first settling tank 31 is introduced to the methane reactor 41 through a pipe 109 for the methane fermentation as described above.

The gas generated in the acid reactor 21 and methane reactor 41 is introduced in a gas storage tank 62 through pipes 201, 202, a desulfurizing device 61 and a pipe 203. The composition of the gas generated in the acid fermentation is mainly 70 to 90% of $CO_2$, 1 to 15% of $H_2$ and minute amounts of $N_2$ and $H_2S$. The gas thus formed in the acid fermentation is used for dilution of a high-calory gas generated at the subsequent methane fermentation step, which is rich in $CH_4$, or is discharged into open air after desulfurization with a ferric salt or utilized effectively after compression.

The composition of the gases generated in the methane reactor 41 is 60 to 90% of methane and 10 to 40% of carbon dioxide gas, and minute amounts of $H_2S$, $N_2$ and $H_2$.

The waste in which has been completed the methane fermentation in the methane reactor 41, is introduced to a third setting tank 51 through a pipe 107 in which the waste is separated by a solid-liquid separation method into a supernatant liquid and a waste sludge. The supernatant liquid is then discharged from the setting tank 51 through a pipe 108 as an effluent after a deprivation of BOD (Biological Oxygen Demand) by a treatment of activated sludge. The waste sludge is withdrawn from the settling tank 51 through a pipe 113 and 114. Usually, it is dehydrated, dried and then used as materials for production of organic fertilizers.

It is preferable to recycle a part of thus separated waste sludge to further enhance the efficiency of the methane fermentation through a pipe 115 and 116, because the reaction speed of the methane fermentation is lower than that of the acid fermentation.

Further, because the waste sludge thus separated includes much of methane formers, it is preferable to recycle the waste sludge to the preliminary treatment tank 12 or the acid reactor 21 through pipes 113, 115, 118, and 117 as raw materials, for the purpose to enhance the gas yield of the system.

In order to enhance the efficiency of the methane fermentation, it is preferable to recycle a part of thus separated waste sludge.

This invention will be further understood from the following examples:

EXAMPLE A 2.5 ml of 35% HCl was added to 490 g of activated sludge (having a solid content of 1.5% and an organic content of 6.1%) from a city sewage disposal plant, so as to adjust the pH to 2.0. The waste was charged in a stainless beaker and heated at 95° C for 5 minutes while agitating. Then, 2.5 ml of 30% NaOH was added to adjust the pH to 5.8 and the waste was charged in a 1 liter capacity glass acid fermentation tank and inoculated with 10 g of a cultured broth obtained by inoculating the preliminary treated sludge having the same concentration as above with acid fermentation bacteria, i.e. Clostridum, Escherichia, Bacillus and Staphyloccus separated from garbage and conducting an anaerobic cultivation at 40° C for 4 days. Then, the acid fermentation was conducted under an anaerobic condition for 3 days at an agitation speed of 150 to 200 rpm at 40° C while automatically adjusting the pH to 5.8. After the acid fermentation, the waste was transferred into a settling tank, and 65 g of the residue having a solid concentration of 20% was separated therefrom. Then, 50 mg of $CaCl_2$ was added to 440 g of the highly turbid supernatant liquid and it was heated at 100° C for 5 minutes to agglomerate the cells of the acid fermentation bacteria, which were then separated in a settling tank. Thus, about 10 g of the cells of the acid fermentation bacteria were recovered. HCl was added to thus recovered cells of the acid fermentation bacteria to adjust the pH to 2.0, and the cells were heated at 95° C for 5 minutes and treated under the same condition as above by using a 100 ml capacity tank. The above supernatant liquid was combined with the undigested residue and the cells which were subjected to the acidifying treatment again, and the mixture was charged in a 1 liter capacity methane fermentation tank and inoculated with 10 g of methane fermentation bacteria, i.e. Metanosarcina, Metanococcus and Metanobacterium cultured in the above supernatant liquid. The anaerobic cultivation was conducted at 40° C and the amount of the digestion gas produced was measured every day.

EXAMPLE B

In a 1 liter capacity glass acid fermentation tank, 490 g of activated sludge having a solid content of 1.6% and an organic content of 6.1% from a city sewage disposal plant was charged, and the activated sludge was inoculated with 10 g of a cultured broth obtained by inoculating sludge having the same concentration as that of the above activated sludge with acid fermentation bacteria separated from garbage, i.e. Clostridum, Escherichia, Bacillus and Staphyloccus and conducting an anaerobic cultivation at 40° C for 4 days. The acid fermentation was conducted at an agitation speed of 150 to 200 rpm and a temperature of 40° C for 3 days while automatically adjusting the pH to 5.8. After the acid fermentation has completed, the waste was transferred to a setting tank to separate therefrom 69 g of an unacidified residue (having a solid content of 19%). Then, 50 mg of $CaCl_2$ was added to the supernatant liquid containing cells of the acid fermentation bacteria suspended therein and was heated at 100° C for 7 minutes to agglomerate the cells of the acid fermentation bacteria. The cells were separated in a settling tank to obtain about 11 g of the cells, and the cells were subjected to the acid fermentation under the same condition as described above by using a 100 ml capacity tank. The supernatant liquid obtained by the acid fermentation was mixed with the unacidified residue and the cells of the acid fermentation bacteria which had been subjected to the acid fermentation again, and the mixture was charged in a 1 liter capacity methane fermentation tank and inoculated with 10 g of a cultured broth of methane fermentation bacteria, i.e. in the same supernatant liquid as mentioned above, and an anaerobic cultivation was conducted at 40° C and the amount of the digestion gas produced was measured every day.

For comparison, experiments of the anaerobic treatment was conducted according to the conventional methods. Following two examples C and D are the result of the conventional methods.

EXAMPLE C

The treatment was conducted according to the conventional two-phase anaerobic method on the same sludge as in the example A. In this example, the waste was subjected to centrifugal separation after acid fermentation at 6,000 G for 5 minutes, and the supernatent liquid from which the residue and cells of acid fermentation bacteria had been withdrawn from the waste was subjected to the methane fermentation.

EXAMPLE D

The treatment was conducted on the same waste as in the example A according to the conventional anaerobic stabilization method in which the waste was treated within a same treatment tank for both the acid fermentation and methane fermentation period.

Figure 4:
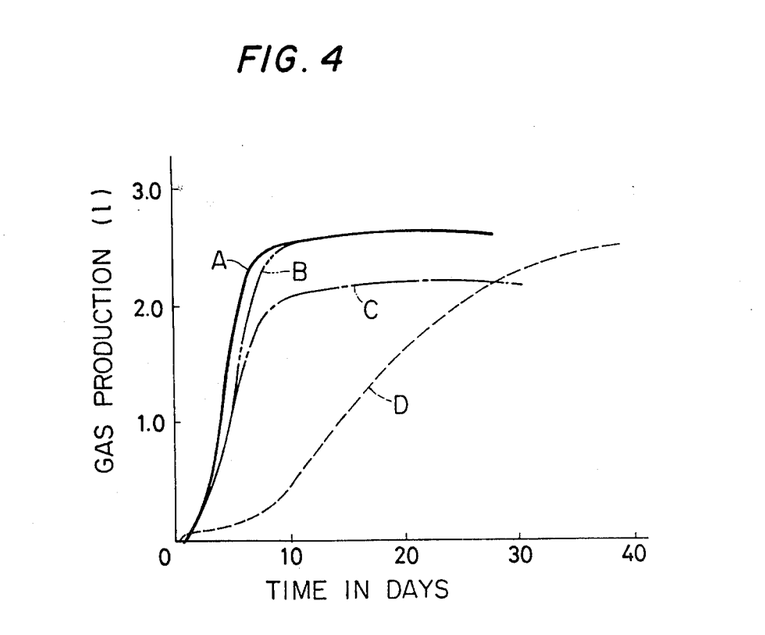
FIG. 4 is a graph showing the experimental results of the gas productivity of the present invention and the prior art methods.

Referring now to FIG. 4 of the drawings, curves A, B, C, and D respectively show the results of the example A, B, C, and D. As apparent from the FIG. 4, the digestion gas productivity and treatment efficiency of the present methods A and B are superior to that of the conventional methods C and D. Further, as apparent from the curves A and B, the gas productivity of the example A in which pretreatment of the waste is conducted before the acid fermentation is superior to that of the example B.

Figure 2:
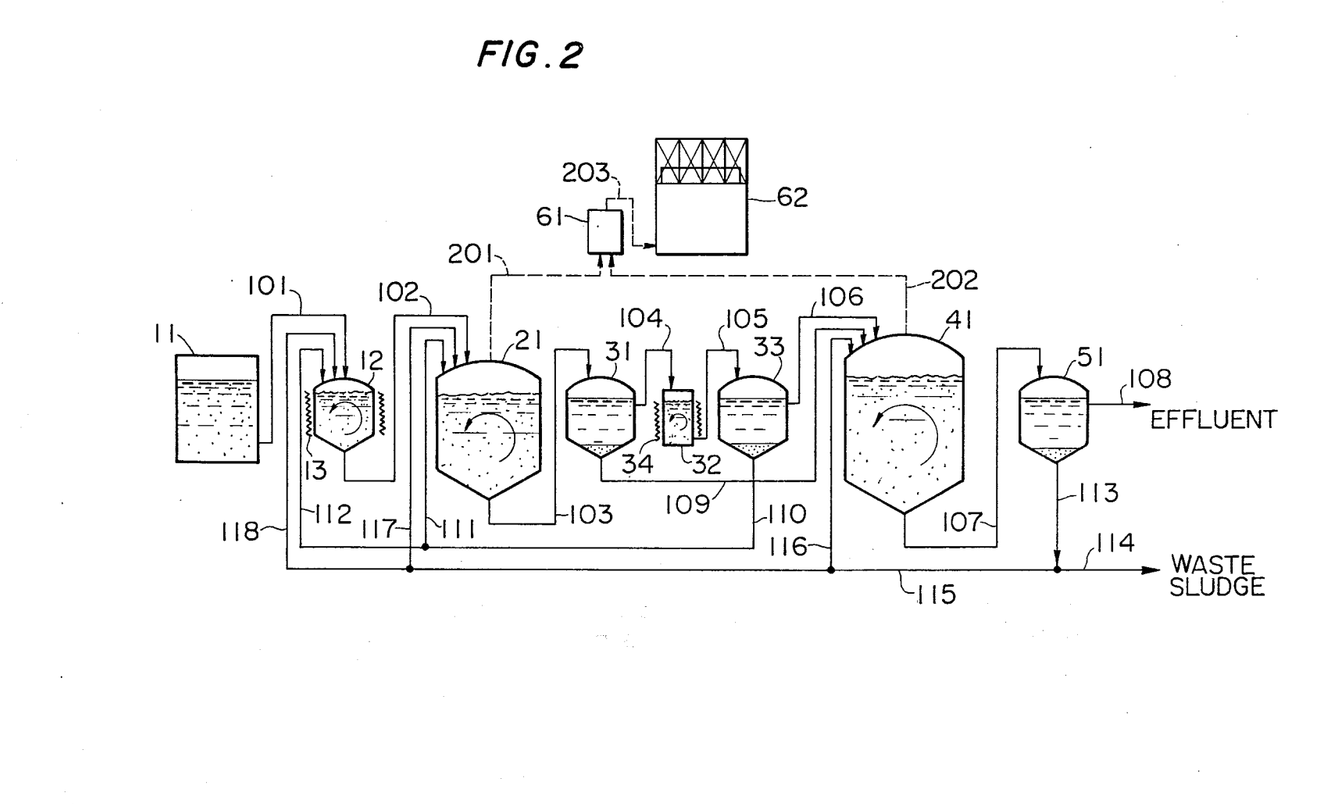
FIG. 2 is a diagrammatic flow sheet illustrating one embodiment of the present invention.
Figure 3:
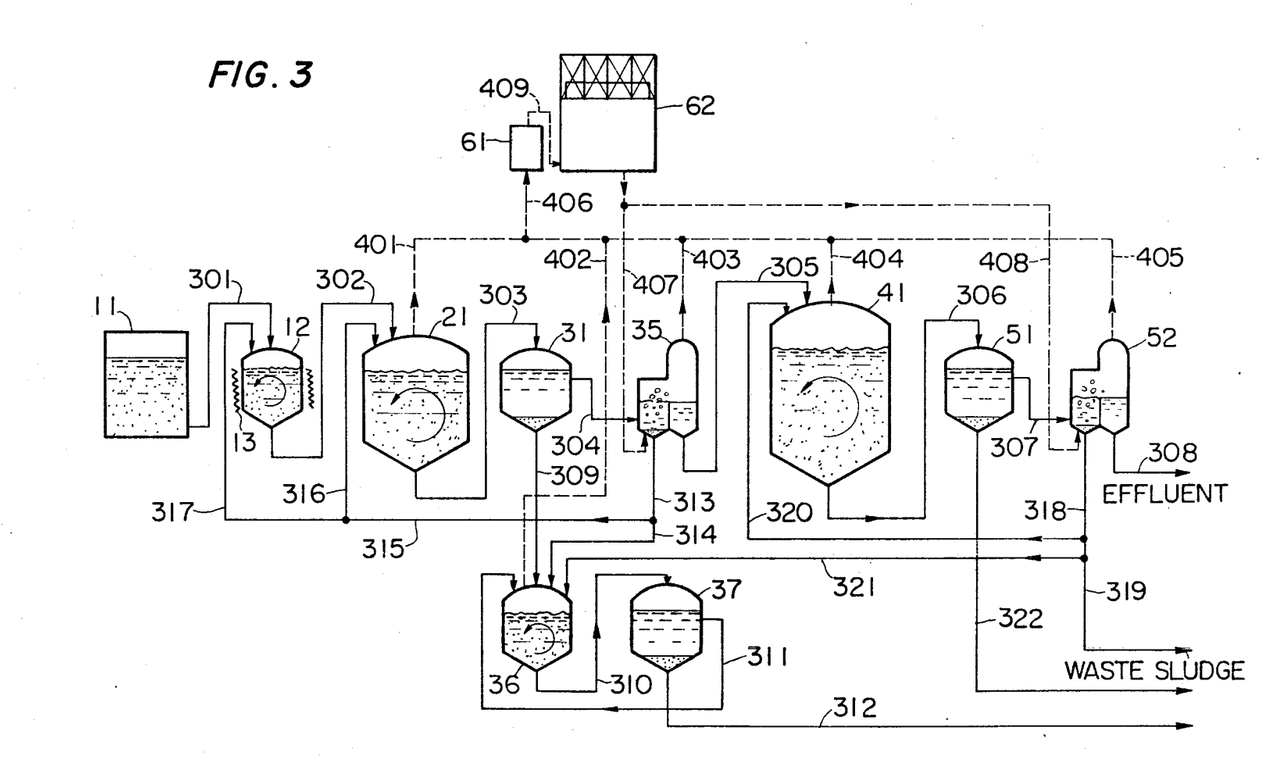
FIG. 3 is a diagrammatic flow sheet illustrating another embodiment of the present invention.

Referring now to FIG. 3 of the drawings, in which the same reference numeral indicates the same function or apparatus as in FIG. 2, biochemical waste stored in a raw material tank 11 is introduced to the pretreatment tank 12 through a pipe 301. As described with respect to FIG. 2, after completed the preliminary treatment of the waste in the pretreatment tank 12, the waste is introduced to the acid reactor 21 for the acid fermentation through a pipe 302. The waste in the acid reactor 21, which contains the unacidified residue the cells of the acid formers and volatile organic acids, is introduced to an unacidified residue settling tank 31 through a pipe 303, in which the cells of acid formers and the volatile organic acids are separated from the unacidified residue by a solid-liquid separation method. As far as the activity of the cells of acid formers are not inhibited, any methods can be employed such as a sedimentation separation, a centrifugal separation using a low speed centrifugal separator for concentration of sludges, and a filtration method. Since the unacidified residue can readily be sedimented by standing for a short period, the intended object can be obtained sufficiently in many cases by the sedimentation separation method.

In such a case that only a little amount of unacidified residue is formed, the settling tank 31 can be omitted.

The unacidified residue thus separated in the settling tank 31 can hardly be acidified any more, and may not be directly discharged from the treatment system because of bad smell, so that the unacidified residue is treated by methane fermentation.

On the other hand, the supernatant liquid including cells of acid formers, are introduced to a bacteria separator 35 through a pipe 304, in which the digestion gas from the gas storage tank 62 is introduced through a pipe 407 to the bottom of the bacteria separator 35. In the bacteria separator 35, there is provided a low wall to partition the separator 35 into first and second chambers. The supernatant liquid introduced in the first chamber is bubbled by the digestion gas introduced through the pipe 407 and bubbles including organic acids are overflown into the second chamber, thereby the cells of acid formers are separated and left in the first chamber. Thus separated cells of acid formers are recycled for further acid fermentation to the pretreatment tank 12 or the acid reactor 21 through pipe 313, 315, 316, 317.

When the operation is conducted continuously for a long period, excessive amount of the acid formers are produced. In this case, the separated acid formers may be directly fed to the methane reactor 41.

The effluent overflown in the second chamber, which contains organic acids and from which the cells of acid formers have been removed, is fed to the methane reactor 41 through a pipe 305 and the organic acids are converted to methane and carbon dioxide gas by methane formers. The preferred conditions of the methane fermentation are the same as described with respect to FIG. 1.

The waste in which has been completed the methane fermentation in the methane reactor 41, is introduced to a settling tank 51 through a pipe 306 in which the waste is separated by a solid-liquid separation method into a supernatant liquid and a waste sludge.

The supernatant liquid including methane formers is then fed to a bacteria separator 52 through a pipe 307, which has the same construction as the bacteria separator 35, wherein the supernatant liquid is separated into waste sludge including methane formers and waste effluent by bubble separating method. The waste effluent is withdrawn through a pipe 308, and the waste sludge including cells of methane formers is partly withdrawn through pipes 318 and 319 and partly recycled to the methane reactor 41 for methane fermentation through pipes 381 and 320.

The waste sludge thus separated in the settling tank 51, which has only a slight sewage smell or ammonia smell, is withdrawn from the treatment system through a pipe 322, dehydrated, dried and can be used as organic fertilizers.

In this embodiment, a methane reactor 36 is employed in addition to the methane reactor 41, which is exclusively used for the methane fermentation of the unacidified residue in the settling tank 31 and the cells of acid formers in the bacteria separator 35.

The unacidified residue in the settling tank 31 can be directly fed to the methane fermentation reactor 41, however, when the unacidified residue has a high solid concentration, it is preferable to treat the unacidified residue in the methane reactor 36 provided in addition to the methane reactor 41 so as to reduce the power consumed for agitation in the reactor 41. The unacidified residue through the pipe 309 and the cells of acid formers through the pipe 314 is mixed with the waste sludge including the cells of methane formers through the pipe 321 and anaerobically treated under the existence of the methane formers. The waste in which has been completed the methane fermentation in the reactor 36 is introduced to a settling tank 37 through the pipe 310. The supernatant liquid thus separated in the settling tank 37 is recycled to the reactor 36 through a pipe 311, repeatedly treated in the reactor 36 and finally withdrawn through a pipe 312 as a waste sludge.

The gas generated in the acid reactor 21, methane reactor 41 and 36 is introduced in a gas storage tank 62 through pipes 401, 402, 404 and 406, a desulfurizing device 61 and a pipe 409. The gas introduced to the bacteria separator 35 and 52 through pipes 407 and 408 is recovered through pipes 403 and 405, and repeatedly used for the bubble separation method.

EXAMPLE E

Activated sludge was first subjected to a preliminary heat treatment under acid condition and thereafter subjected to an anaerobic treatment. The preliminary treatment was conducted in the following manner.

25 ml of 35% hydrochloric acid was added to 5 Kg of activated sludge having a solid content of 3.0% and an organic content of 2.1% while agitating and adjusting the pH to 2.0. The waste was charged in a stainless heating tank equipped with an agitator, and maintained at 95° C for 5 minutes. The waste was then cooled to 40° C and fed to an acid fermentation tank by 30 g/l/day, which tank has an effective capacity of 10 l and equipped with an agitator and an automatic pH adjuster. The acid fermentation was conducted continuously under conditions of an agitating speed of 200 rpm, a temperature of 40° C, a pH of 5.8 (adjusted by feeding Na OH solution) and a residence time of 40 days. As seed bacteria, i.e. Clostridium, Escherichia, Bacillus and Staphyloccus the acidified sludge obtained by conducting the acid fermentation under the above conditions for at least 2 weeks was used.

The acidified waste was introduced into a settling tank having an effective capacity of 0.5 l and stayed therein for 3.8 hours, whereby it was separated into the unacidified residue and the liquid portion. All of the unacidified residue was fed to a methane fermentation tank described below. Cells of the acid fermentation bacteria in the liquid left after the separation were separated and concentrated according to the following method. 300 ml of the liquid was charged into a first glass cylinder having a diameter of 3.6 cm and a length of 1 m, and nitrogen gas was blown into the liquid at a rate of 3 /min for about 10 minutes from a nozzle having a diameter of 0.5 mm and disposed on the bottom of the first cylinder by using a pump. Bubbles rising in the first cylinder and overflown therefrom were introduced into a second glass cylinder, which has a capacity of 2 liters and is connected horizontally to the top of the first glass cylinder through a glass tube having a diameter of 3.6 cm. Thus, 250 ml of acidified effluent was obtained in the second glass cylinder with the overflown bubbles. On the other hand, the concentration of cells of acid fermentation bacterias in the first glass cylinder was increased to 5 times as that before separation of the bubble method. Thus obtained liquid including cells of acid fermentation bacteria were recycled to the acid fermentation tank at a rate of 4 g/l/day. The remaining liquid including cells of acid fermentation bacteria was subjected to the pretreatment and recycled to the acid fermentation tank.

The acidified effluent in the second glass cylinder was introduced to a methane fermentation tank having an effective capacity of 20 liters, where the effluent was treated by the methane fermentation. The methane fermentation tank was equipped with an agitator and an automatic pH adjuster. The methane fermentation was conducted therein under condition of a residence time of 8 days, a temperature of 40° C and a pH of 7.5 (adjusted by feeding HCl solution). The amounts of gas produced by the acid and the methane fermentation were measured from the amount of the saline solution overflown in the gas storage tank As the seed bacteria, i.e. Metanosarcina, Metanococcus and Metanobacterium for the methane fermentation, a digested sludge formed by performing the methane fermentation continuously for at least 2 weeks was employed. The liquid in which the methane fermentation had been completed was introduced into a settling tank having an effective capacity of 0.5 liter and made resident therein for 3.8 hours, whereby the liquid was separated into the undigested residue and the liquid containing cells of the methane fermentation bacterias. The cells of the methane fermentation bacterias in the liquid were separated and concentrated by the same bubble method as employed after the acid fermentation. As a result of the bubble method there are 260 ml of effluent including the cells of methane fermentation bacterias. The concentration of the cells of the methane fermentation bacteria in the effluent was increased to about 5 times as that before separation of the bubble method. The effluent was recycled to the methane fermentation tank at a rate of 4 g/l/day as the organic material. The remaining cells were subjected to the preliminary treatment and then fed to the acid fermentation tank at a rate of 1.0 g/l/day.

According to the above experiments, it was found that the digestion ratio was 70.5% the gas yield was 538 ml per g of the organic material and the content of the gas was 72% of $CH_4$ and 27% of $CO_2$.

What is claimed is:

1. A process for anaerobic digestion of waste containing relatively high molecular weight organic materials comprising;

a first step of anaerobically digesting the waste by bacterial acid formers in an acid fermentation reactor to convert the high molecular weight organic materials into low molecular weight organic materials and further to convert the low molecular weight organic materials into volatile organic acids, a second step of separating the waste in said first step into a first portion containing volatile organic acids and a second portion containing undigested residue and cells of the acid formers, a third step of anaerobically digesting the first portion by bacterial methane formers in a methane fermentation reactor separate from said acid fermentation reactor to generate methane and carbon dioxide gas, a fourth step of separating the waste in said third step into a third portion containing digested sludge and effluent and a fourth portion containing cells of methane formers, and a fifth step of partially recycling the second portion separated in said second step in order to digest within at least one of the reactors effecting the anaerobic digestion steps.

2. The process according to claim 1, wherein said fifth step comprises a step of recycling a part of the second portion separated in said second step to the reactor effecting said first step and further comprises a sixth step wherein the remaining of the second portion is introduced into the reactor effecting said third step.

3. The process according to claim 2, wherein a part of the fourth portion containing cells of methane formers is recycled to a reactor effecting said third step and the remaining of the fourth portion is withdrawn as waste sludge.

4. The process according to claim 1, wherein the process further includes a step of pretreating the waste prior to said first step by adding acid to the waste to adjust a pH thereof below 3.5 and heating to a temperature of 60° to 200° C for a predetermined period, and thereafter by adding alkali to neutralize the resulting waste.

5. The process according to claim 4, wherein a part of the second portion separated in said second step is recycled to said pretreating step and the remaining of the second portion is introduced to a reactor effecting said third step, and the fourth portion separated in said fourth step is recycled to a reactor effecting said third step.

6. The process according to claim 5, wherein said second step comprises the steps of;
 a. separating the waste in said first step into a supernatant liquid containing cells of acid formers and volatile organic acids, and a solid waste containing undigested sludge,
 b. heating the supernatant liquid to physiologically deactivate the acid formers,
 c. and again separating thus heated supernatant liquid into a supernatant liquid containing undigested sludge and a solid waste containing the deactivated cells of acid formers.

7. The process according to claim 3, wherein said second step comprises the steps of;
 a. separating the waste in said first step into a supernatant liquid containing cells of acid formers and volatile organic acids, and a solid waste containing undigested sludge,
 b. heating the supernatant liquid to physiologically deactivate the acid formers,
 c. and again separating thus heated supernatant liquid into a supernatant liquid containing undigested sludge and a solid waste containing the deactivated cells of acid formers.

8. The process according to claim 5, wherein said second step comprises the steps of;
 a. separating the waste in said first step into a supernatant liquid containing the cells of acid formers and volatile organic acids, and a solid waste containing undigested sludge, and
 b. separating thus separated supernatant liquid by blowing air therein into a supernatant liquid containing undigested sludge, and a solid waste containing the cells of acid formers.

9. The process according to claim 3, wherein said second step comprises the steps of;
 a. separating the waste in said first step into a supernatant liquid containing cells of acid formers and volatile organic acids, and a solid waste containing undigested sludge, and
 b. separating thus separated supernatant liquid by blowing air therein into a supernatant liquid containing undigested sludge, and a solid waste containing the cells of acid formers.

10. The process according to claim 8, wherein said fourth step comprises the steps of;
 a. separating the waste digested in said third step into a supernatant liquid containing the cells of methane formers, and a solid waste containing undigested sludge,
 b. and separating thus separated supernatant liquid by blowing air therein into a supernatant liquid containing undigested sludge and a solid waste containing the cells of methane formers.

11. The process according to claim 9, wherein said fourth step comprises steps of
 a. separating the waste digested in said third step into a supernatant liquid containing the cells of methane formers, and a solid waste containing undigested sludge,
 b. and separating thus separated supernatant liquid by blowing air therein into a supernatant liquid containing undigested sludge and a solid waste containing the cells of methane formers.

12. The process according to claim 10, which further includes a step of anaerobically digesting the undigested sludge separated in said second and fourth steps, by methane formers to generate methane and carbon dioxide gas.

13. A system for anaerobic digestion of waste containing relatively high molecular weight organic materials comprising;
 an acid reactor in which the waste is anaerobically digested by bacterial acid formers to convert the high molecular weight organic materials and further to convert the low molecular weight organic materials into volatile organic acid,
 a first separator in which the waste in said acid reactor is separated into a first portion containing volatile organic acids and a second portion containing undigested residues and cells of the acid formers,
 a methane reactor separate from the acid reactor for anaerobically digesting the first portion by bacterial methane formers to generate methane and carbon dioxide gas,
 a second separator in which the waste in said methane reactor is separated into a third portion containing digested sludge and effluent and a fourth portion containing cells of the methane formers, and
 means for partially recycling the second portion separated in said first separator in order to digest the recycled second portion within the anaerobic digesting system.

14. The system according to claim 13, wherein said means recycles a part of the second portion to said acid reactor and further comprising another means for introducing the remaining of the second portion to said methane reactor.

15. The system as recited in claim 14, further comprising;
 means for recycling a part of the fourth portion containing cells of the methane formers to said methane reactor and withdrawing the remaining of the fourth portion as waste sludge.

16. The system as recited in claim 13, further comprising;

a pretreatment tank in which the waste is treated prior to said acid reactor by adding acid to the waste to adjust a pH thereof below 3.5 and heating to a temperature of 60° to 200° C for a predetermined period thereafter adding alkali to neutralize the waste.

17. The system as recited in claim 16, wherein said first separator comprises;
  a. a first means for separating the waste in said acid reactor into a supernatant liquid containing cells of acid formers and volatile organic acids, and a solid waste containing undigested sludge,
  b. a second means for heating the supernatant liquid to physiologically deactivate the acid formers, and
  c. a third means for separating thus heated supernatant liquid into a supernatant liquid containing undigested sludge and a solid waste containing the deactivated cells of acid formers.

18. The system as recited in claim 16, wherein said first separator comprises;
  a. a first means for separating the waste in said acid reactor into a supernatant liquid containing cells of acid formers and volatile organic acids, and a solid waste containing undigested sludge, and
  b. a second means for separating the supernatant liquid by blowing air therein into a supernatant liquid containing undigested sludge, and a solid waste containing the cells of acid formers.

19. The process according to claim 1, wherein the undigested residue in the second portion is anaerobically digested in a methane fermentation reactor.

20. The process according to claim 19, wherein the cells of the acid formers are anaerobically digested in the acid fermentation reactor.

21. The process according to claim 19, wherein a portion of the cells of the acid former are anaerobically digested to the methane fermentation reactor in which the undigested residue is further digested.

22. The process according to claim 19, wherein the undigested residue and the cells of the acid formers are digested in a methane fermentation reactor in which the first portion is digested.

* * * * *